US011793463B2

(12) United States Patent
Li Tak Cheung

(10) Patent No.: US 11,793,463 B2
(45) Date of Patent: Oct. 24, 2023

(54) MULTI-ZONE PRESSURE SENSITIVE MAT WITH TWO ELECTRODES

(71) Applicant: EVISION TECHNOLOGY LIMITED, Kowloon (HK)

(72) Inventor: Cooper Li Tak Cheung, Kowloon (HK)

(73) Assignee: VJ Electronics Limited, Hong Kong (HK)

( * ) Notice: Subject to any disclaimer, the term of this patent is extended or adjusted under 35 U.S.C. 154(b) by 487 days.

(21) Appl. No.: 17/143,511

(22) Filed: Jan. 7, 2021

(65) Prior Publication Data
US 2022/0211326 A1    Jul. 7, 2022

(51) Int. Cl.
| G01L 1/00 | (2006.01) |
| A61B 5/00 | (2006.01) |
| A61B 5/11 | (2006.01) |
| G01L 1/20 | (2006.01) |
| G16H 40/67 | (2018.01) |

(52) U.S. Cl.
CPC .......... *A61B 5/6892* (2013.01); *A61B 5/1115* (2013.01); *A61B 5/725* (2013.01); *A61B 5/7225* (2013.01); *G01L 1/205* (2013.01); *A61B 2560/0223* (2013.01); *A61B 2562/0247* (2013.01); *A61B 2562/046* (2013.01); *A61B 2562/227* (2013.01); *G16H 40/67* (2018.01)

(58) Field of Classification Search
CPC ... A61B 5/6892; A61B 5/1115; A61B 5/7225; A61B 5/725; A61B 2560/0223; A61B 2562/0247; A61B 2562/046; A61B 2562/227; G01L 1/205; G16H 40/67
See application file for complete search history.

(56) References Cited

U.S. PATENT DOCUMENTS

| 4,382,227 A * | 5/1983 | Olivenbaum .......... G01R 15/09 324/123 R |
| 2005/0070827 A1* | 3/2005 | Lee ..................... A61H 23/0263 601/57 |
| 2014/0267152 A1* | 9/2014 | Curtis .................... G06F 3/0445 345/174 |
| 2017/0188875 A1* | 7/2017 | Banet .................... A61B 5/0537 |
| 2019/0117124 A1* | 4/2019 | Hsu ....................... A61B 5/6892 |
| 2019/0286263 A1* | 9/2019 | Bagheri ................ G06F 3/0414 |
| 2023/0100129 A1* | 3/2023 | Vaze .................... G06F 3/04164 345/173 |

* cited by examiner

*Primary Examiner* — Max H Noori

(57) ABSTRACT

The present invention discloses a multi-zone pressure sensitive mat comprises a first electrode and a second electrode, wherein: the first electrode connects to an input port of a central processing unit and the second electrode connects to the digital ground return port of the central processing unit; the central processing unit comprises at least one MCU, the MCU comprises a first ADC unit and a second ADC unit, wherein electrical signal form the input port is split into original DC signal and its AC signal, wherein the DC signal is fed into the first ADC unit from the input port, the AC signal is bypassed through a capacitor from the input port, filtered through a LPF, amplified through an amplifying circuit and fed into the second ADC unit; wherein a preset threshold voltage level and a preset interval of time are stored in the MCU; the MCU detects the presence, the absence and the movement of human on bed by measuring voltage value from output port of the first ADC unit and amplitude of the AC signal from output port of the second ADC unit.

19 Claims, 3 Drawing Sheets

MULTI-ZONE PRESSURE SENSITIVE MAT WITH TWO ELECTRODES

FIELD OF THE INVENTION

The present invention generally relates to a pressure sensor and particularly to a low cost and durable multi-zone pressure sensitive mat with two electrodes for detecting the presence, the absence and the movement of human on bed.

BACKGROUND OF THE INVENTION

It is important in several applications to monitor whether a user or patient is in their bed, or whether the user or patient has got up and left their bed. The most prominent applications are the care of the elderly, care of children and care of patients with specific conditions or circumstances. For example, there are high needs to leave the bed for lavatory among the elderly during bedtime. Hospitalized patient stays on the bed a much longer time, they have the same needs for leaving bed. These persons suffer from increase in falls and accidents during bedtime. Abnormal extend of rest time without movement or inactivity may be hazardous. Therefore, it is essential for caregivers to be alerted for any abnormal activity and for any abnormal inactivity, enabling caregivers to provide rapid response to these safety issues.

There are several devices available that can detect when a patient has left the bed. Usually, these devices use either pressure switches or pressure sensitive sensor mats to measure the pressure or load on the bed. In general, an alarm is triggered when the measured pressure falls below a predefined threshold. The valid logic signal depends so much on the effective resistance of the sensor circuit. Conductive carbon ink of low resistance value is high at cost. Furthermore, oxidation and ageing effect increase the resistance of the sensor circuit over the time of usage. Pressure sensitive sensor mat comes to an end of its lifespan when the overall resistance reaches a threshold that the logic level is undetermined. General multi-zone pressure sensitive sensor mat consists of number greater than 2 electrodes, number of electrodes of this type of sensor mat is in direct proportion to the number of sensor zones of it. Power consumption and the overall cost of these devices increases along with additional number of electrodes.

Despite of substantial variation and great effort by practitioners of the monitor arts in providing ever more accurate and reliable indication of whether the patient on the bed, there remains nonetheless a continuing need for improved the pressure sensitive sensor mat.

SUMMARY OF THE INVENTION

One object of the present invention is to provide a multi-zone pressure sensitive mat with only two electrodes connect to a central processing unit which dispatch alarm of various abnormal conditions according to the presence or absence of pressure on one or multiple pressure sensor zones. By using the measurement of voltage level derived from a relative variable resistance circuit, lifespan of the multi-zone pressure sensitive sensor mat is extended a great deal.

To achieve the above object, the present invention provides a multi-zone pressure sensitive mat comprises a first electrode and a second electrode, wherein: the first electrode connects to an input port of a central processing unit and the second electrode connects to the digital ground return port of the central processing unit; the central processing unit comprises at least one micro controller unit (MCU), the MCU comprises a first analog to digital conversion (ADC) unit and a second ADC unit, wherein electrical signal from the input port is split into original direct current (DC) signal and its alternating current (AC) signal, wherein the DC signal is fed into the first ADC unit from the input port, the AC signal is bypassed through a capacitor from the input port, filtered through a low pass filter (LPF), amplified through an amplifying circuit and fed into the second ADC unit; wherein a preset threshold voltage level and a preset interval of time are stored in the MCU; the MCU detects the presence of human by measuring voltage value from output port of the first ADC unit which is below the preset threshold voltage level of open circuit condition and lasts for the preset interval of time; the MCU detects the absence of human by measuring voltage value from output port of the first ADC unit which returns to the preset threshold voltage level of open circuit condition and lasts for the preset interval of time; the MCU detects the movement of human by voltage value from output port of the first ADC unit which is below the preset threshold voltage level of open circuit condition and measures amplitude of the AC signal from output port of the second ADC unit; the MCU detects the voltage value from output port of the first ADC unit which is within the preset threshold voltage level of open circuit condition, the calibration is required.

In one embodiment, the multi-zone pressure sensitive mat comprises a multi-zone passive pressure sensor, wherein the passive pressure sensor comprises a top sensors matrix, a middle flexible insulation spacer and a bottom sensors matrix, wherein the top sensors matrix is a top layer of variable resistance sensors row matrix and the bottom sensors matrix is a bottom layer with variable resistance sensors column matrix; the top sensors matrix and the bottom sensors matrix are comprised of a flexible thermoplastic membrane serves as a substrate for an electrical circuit, and the electrical circuit on the top sensor matrix and the bottom sensor matrix are comprised of electrical tracks, embedded resistors and variable resistance sensor nodes.

In one embodiment, the variable resistance sensor node is comprised of a top contact pad and a bottom contact pad, the top contact pad and the bottom contact pad are fabricated by printing with Polymer Thick Film (PTF) carbon ink of same uniform composition over the whole printed circuit, and a corresponding opening on middle flexible spacer allows the top contact pad comes into electrically contact with the bottom contact pad; effective value of resistance of each variable resistance sensor node is in indirect proportion to the area of physical contact between the top contact pad and the bottom contact pad.

General type of pressure sensitive sensor mat detects the presence of a weight by reading the binary logic signal of a sensor node from the closure status of such sensor node. Valid logic signal depends so much on the effective resistance of the sensor circuit. Conductive carbon ink of low resistance value is high at cost. Furthermore, oxidation and ageing effect increase the resistance of the sensor circuit over the time of usage. The pressure sensitive sensor mat comes to an end of its lifespan when the overall resistance reaches a threshold that the logic level is undetermined. The present invention detects the presence of user or patient through measuring the analog voltage level of the sensor circuit, hence the comparatively higher cost conductive carbon ink of low resistance value can be substituted by lower cost conductive carbon ink, while maintaining accuracy and sensitivity of the sensor throughout a much longer life span.

All types of pressure sensitive sensor mat which consists of conductive carbon ink suffer from ageing, oxidation over the usage. The overall resistance of the circuit increases as a result of mechanical wear out on the exposed contact node of such sensor mat. General type pressure sensitive sensor mat works along with alarm system using complementary metal oxide semiconductor (CMOS) technology with a logic low threshold at 0.8V in closed circuit condition. The sensor mat comes to the end of its life when the overall resistance reaches a threshold value that constitutes invalid logic signal, above 0.8V, in close circuit condition. The present invention measures analog voltage level derived from a relative resistance of the sensor circuit instead of a discrete logic level. The initial closed circuit voltage level, as a ground reference voltage, is registered in a nonvolatile memory during the manufacturing process. Users or service attendants may carry out a simple build-in calibration routine to refresh the in-system memory with the new ground reference voltage level. This ground reference voltage rises through the usage of the sensor mat, as a result of ageing, oxidation and mechanical wear out. The present invention tolerates ground reference voltage as high as 2.5V in 3.3V system using CMOS technology, three folds extended effectiveness in comparing with the general type sensor mat. Regular calibration of this reference voltage retains the sensitivity and effectiveness of the sensor mat throughout the extended life span of the sensor mat.

General multi-zone pressure sensitive sensor mat consists of number greater than 2 electrodes, number of electrodes of this type of sensor mat is in direct proportion to the number of sensor zones of it. Power consumption and the overall cost of these devices increases along with additional number of electrodes. The present invention uses only two electrodes to connect to two high impedance input ports of the host microcontroller. With these two electrodes, it facilitates up to 36 individual sensor zones in a single unified sensor mat assembly. The present invention reduces a great deal of cost in terms of hardware and assembling.

General multi-zone pressure sensitive sensor mat detects patient's movement by measuring the logic level of each individual sensor node. This method requires the weight to be removed completely from a sensor node so that a valid logic level can be asserted. The present invention implements a secondary AC signal path which it can extract the AC components from the fundamental analog signal, and it amplifies the AC signal to the level that the host microcontroller be able to detect slight movement. Movement over each variable resistance sensor node alters the effective resistance of such sensor node, hence, generates small AC signal which is modulated over the fundamental analog signal. The present invention detects slight activity of the patient. It facilitates the system to track patient's health conditions like sleeping quality. These important features empower the system to alert for various hazardous health conditions like seizures, extended immobility.

BRIEF DESCRIPTION OF THE DRAWINGS

To better understand the nature and advantages of the present invention, reference should be made to the following description and the accompanying figures. It is to be understood, however, that each of the figures is provided for the purpose of illustration only and is not intended as a definition of the limits of the scope of the present invention. Also, as a general rule, and unless it is evident to the contrary from the description, where elements in different figures use identical reference numbers, the elements are generally either identical or at least similar in function or purpose.

DETAILED DESCRIPTION OF THE INVENTION

Figure 1:
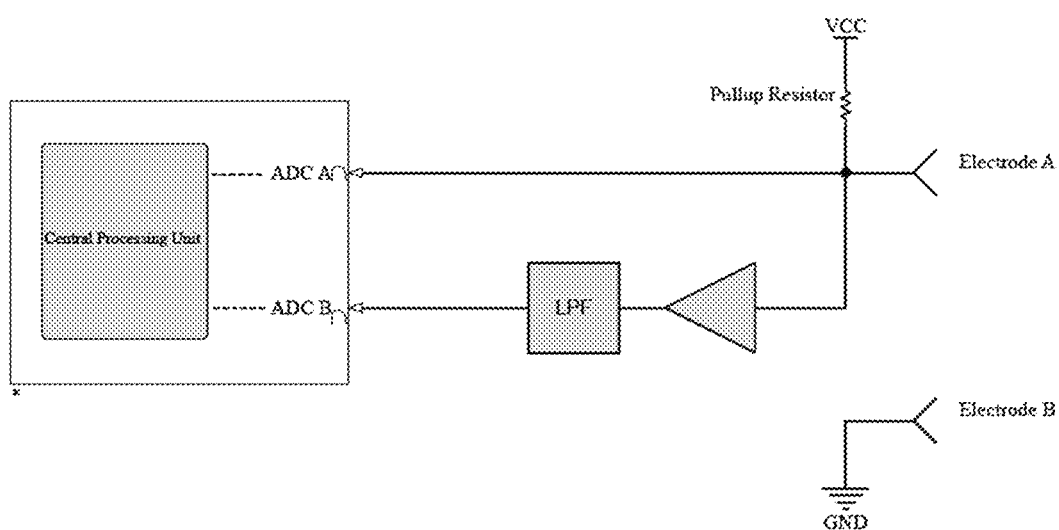
FIG. 1 is a schematic diagram of a multi-zone pressure sensitive sensor mat according to the present invention.

The present invention would be further described herein with reference to the accompanying drawings and embodiments of the present invention. While example embodiments may include various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the claims. Like numbers refer to like elements throughout the description of the figures.

It is to be understood that terms such as "left," "right," "top," "bottom," "front," "rear," "side," "height," "length," "width," "upper," "lower," "interior," "exterior," "inner," "outer" and the like as may be used herein, merely describe points or portions of reference and do not limit the present invention to any particular orientation or configuration. Further, terms such as "first," "second," "third," etc., merely identify one of a number of portions, components and/or points of reference as disclosed herein, and do not limit the present invention to any particular configuration or orientation.

Referring to FIGS. 1-4, the present invention discloses a multi-zone pressure sensitive sensor mat with two electrodes, for example a first electrode (Electrode-A) and a second electrode (Electrode-B), connect to a central processing unit which dispatch alarm of various abnormal conditions according to the presence or absence of pressure on one or multiple pressure sensor zones.

The passive pressure sensor comprises a top layer of variable resistance sensors row matrix (herein after called top sensors matrix), a middle flexible insulation spacer and a bottom layer with variable resistance sensors column matrix (herein after called bottom sensors matrix). The 3-layers functional sensor assembly is encapsulated in a soft, flexible and water proof pouch.

Both the top sensors matrix and the bottom sensors matrix are comprised of a flexible thermoplastic membrane serve as a substrate for the electrical circuit. In one embodiment, the flexible thermoplastic membrane is polyethylene terephthalate (PET) sheet, but not limited to this.

Electrical tracks, embedded resistors and the conductive pattern of sensor nodes are printed over the substrate. Accordingly, the electrical circuit on both the top sensor matrix and the bottom sensor matrix are comprised of electrical tracks, embedded resistors and variable resistance sensor nodes. The electrical circuit is formed by printing the whole pattern of the circuit using a uniform layer of PTF carbon ink over the substrate.

The value of resistance of a particular segment of printed PTF carbon track is specified by the effective length and the overall width of the pattern of the track. An embedded resistor with specific resistance value is fabricated by printing a continuous PTF carbon track or a combination of multiple PTF carbon tracks over the substrate.

The present invention works on a wide range of resistance value of both the individual sensor node and the overall circuit. Resistance value of each sensor node falls within a range from 100 ohm up to 30K ohm. The resistance value of the overall circuit falls within a range from 1.5K ohm to 500K ohm. Resistance of a particular segment of printed PTF carbon track follows the below equation:

$$Rt=Rs(L/W)^2$$

wherein:
Rt is Resistance of the track segment in [Ω];
Rs is Sheet Resistivity in [Ω/mm$^2$], this is a characteristic constant of a specific carbon ink;
L is Length in [mm];
W is Width in [mm].

Both ends of the printed pattern of PTF carbon tracks serve as the terminals of the effective embedded resistor. Embedded resistors connect to the printed circuit with PTF carbon ink of same uniform composition over the whole printed circuit.

A variable resistance sensor node is comprised of a top contact pad and a bottom contact pad. Both the top contact pad and the bottom contact pad are fabricated by printing a solid filled or a mesh pattern, of circular or rectangular shape, with PTF carbon ink of same uniform composition over the whole printed circuit. A corresponding opening on the middle flexible spacer of same size and shape with it centre location aligned with both of the contact pads allows the top contact pad comes into electrically contact with the bottom contact pad, when weight or pressure is applying on the area of the corresponding opening. Consequently, the close circuit condition is asserted and thus an analog voltage level is asserted according to the particular sensor node of the sensor matrix, as well as the percentage of the area being covered by the weight.

The effective value of resistance of each sensor node is in indirect proportion to the area of physical contact between the top contact pad and the bottom contact pad. The area of physical contact is in direct proportion to the portion of the sensor node being covered by the subject human body part. Hence the effective value of resistance of each sensor node is in indirect proportion to the portion of it being covered by the subject human body part.

The central processing unit is comprised of and is not limited to, one or more micro controller units (MCU) with multiple of built-in analog to digital conversion units (hereinafter called ADC Unit), a wireless network controller which can connect to internet service through a local or public WiFi network, and an additional wireless controller which can connect the local caregiver through a local Bluetooth network.

FIG. 1 denotes the equivalent electrical circuit of the multi-zone pressure sensitive sensor mat. Electrode A connects to the input port of the central processing unit. Electrode B connects to the digital ground return port of the host signal processing unit.

Furthermore, in the central processing unit, electrical signal from the input port is split into the original DC signal and the AC component. The original DC signal is fed into one of the analog to digital conversion unit of the MCU (hereinafter called ADC-A, i.e. a first ADC) directly from the input port. The AC signal component is bypassed through a capacitor from the input port, it is filtered and is amplified through a LPF (low pass filter) and amplifying circuit. The filtered AC signal is then fed into another one of the analog to digital conversion unit of the MCU (hereinafter called ADC-B, i.e. a second ADC).

The MCU detects the presence of human through measuring the voltage level from the output of ADC-A. Any voltage level below a preset threshold of open circuit condition, lasting for a preset interval of time, represents the presence of a human. An open circuit voltage level is defined in the hardware circuit with a pull-up resistor connecting the ADC-A input to the power supply of the circuit, under the condition that the circuit between ADC-A and the ground is opened (the top contact pad and the bottom contact pad of all sensor nodes are electrically isolated). The open circuit voltage is usually set to 95% of the voltage of the power supply. The value of this open circuit voltage is registered in a non-volatile memory location of the MCU during a calibration routine in the manufacturing process. Furthermore, the threshold value of open circuit condition is defined as 90% of the value of the open circuit voltage. This calibrated threshold value is registered in a specific location in a non-volatile memory of the MCU. The MCU determines the absence of human through detecting condition that the voltage level of the output of ADC-A returns to the level or above the level of the preset voltage of open circuit, and the voltage level stays for a preset interval of time. The preset interval of time for both to determining presence of human and to determining absence of human is a pre-defined value in milliseconds. The MCU filters out noisy signal by monitoring the consistency of the measured voltage level from input ADC-A. Signal with fluctuation along the preset threshold value of open circuit condition will be ignored.

The MCU detects movement of the human on bed by measuring the amplitude of the AC signal from the output of ADC-B. The AC signal component is derived from the change of resistance of each sensor node.

Figure 2:
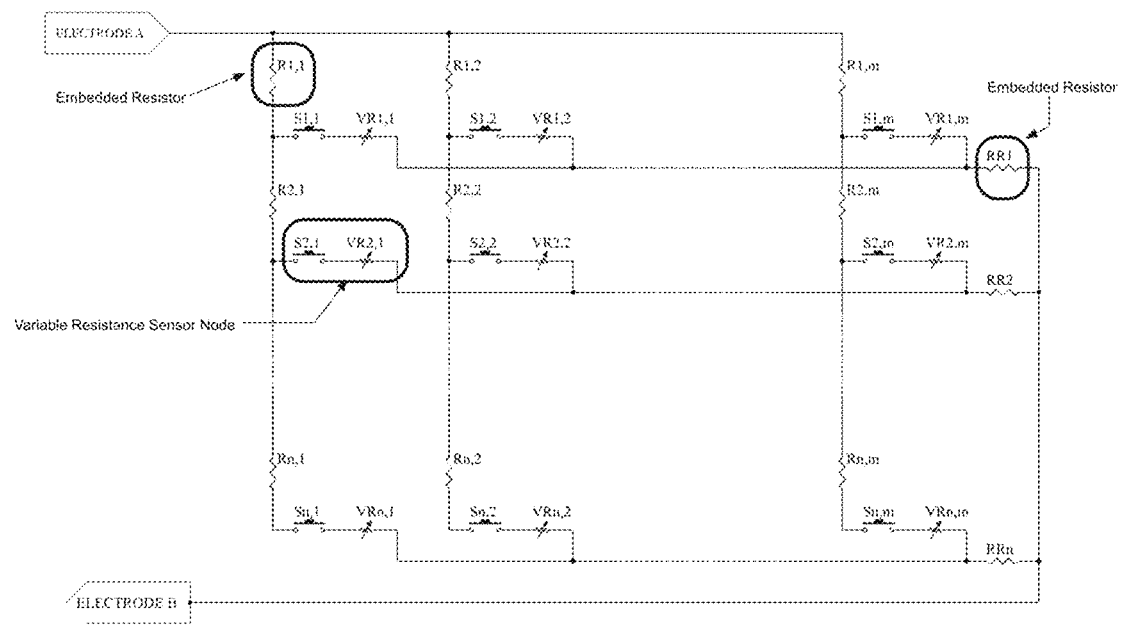
FIG. 2 is a circuit diagram of the multi-zone passive pressure sensor with a two wires interface according to the present invention.
Figure 3:
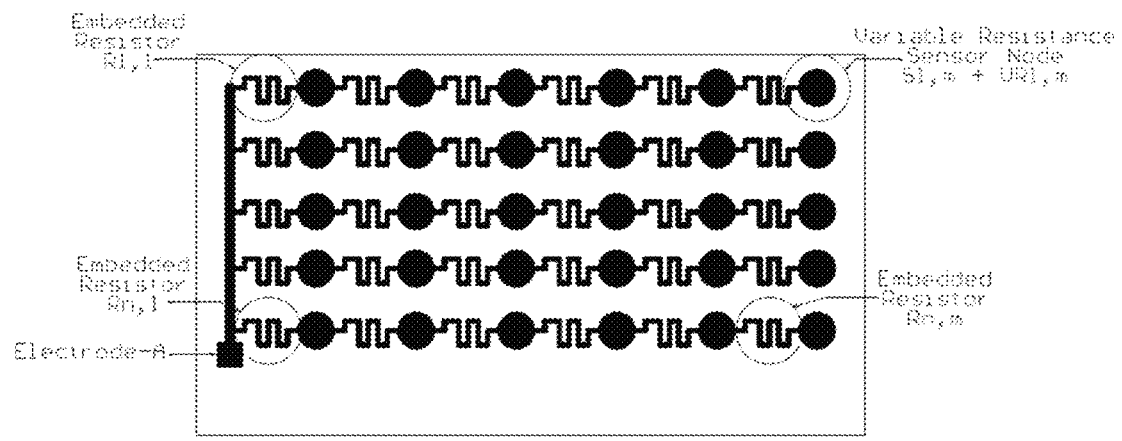
FIG. 3 is a partial circuit diagram of the Electrode-A interface with embedded resistors and variable resistance sensor node according to the present invention.
Figure 4:
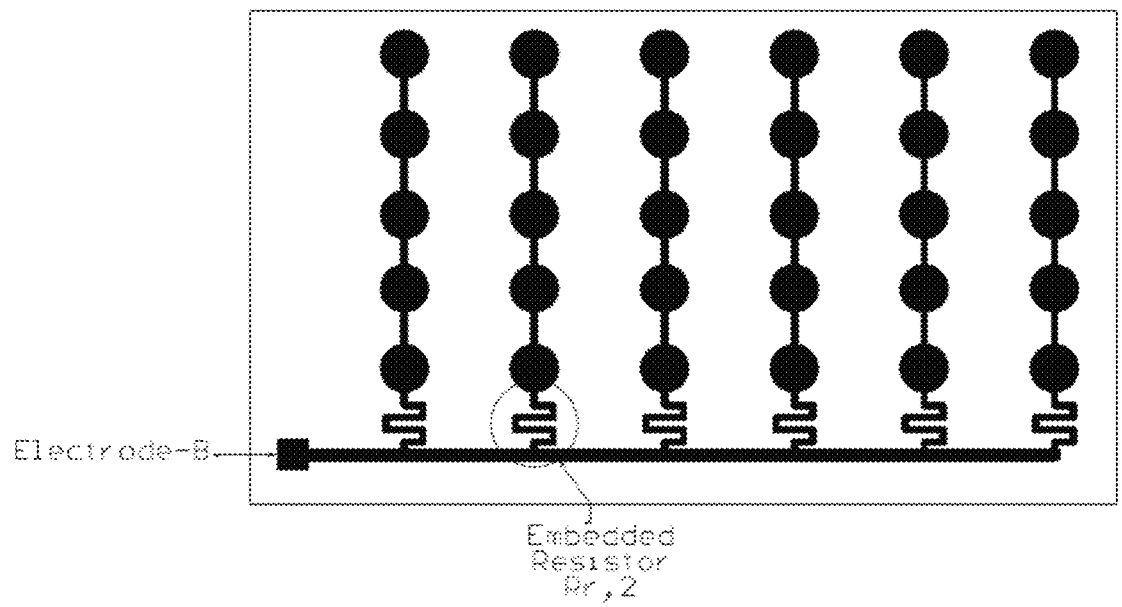
FIG. 4 is a partial circuit diagram of the Electrode-B interface with embedded resistors according to the present invention.

The electrical circuit as described above, is equivalent to a singular variable resistor when any one or multiple of the sensor nodes come into electrical contact. FIG. 2 depicts an equivalent voltage divider circuit comprising a pull-up resistor and such equivalent variable resistor connects across electrode A and electrode B. Voltage across electrodes of the sensor mat, when the sensor mat is connected to the host MCU circuit, is derived by the below formula:

$$V(sensor)=Vcc(R(sensor\ mat)/(R(pull-up)+R(sensor\ mat)))$$

wherein:
V(sensor)=Input voltage to the ADC-A across the two electrodes of the sensor mat;
Vcc=Voltage supply to the central processing unit. One end of the pull-up resistor ties to this voltage;
R(pull-up)=Resistance of the pull-up resistor;
R(sensor mat)=Resistance across electrodes of the sensor mat.

Both the value of Vcc and the value of R(pull-up) are fixed values in the present invention, hence V(sensor) changes along with the change of the effective resistance of the sensor mat which is denoted as R(sensor mat) in the formula above. R(sensor mat) changes along with the change of effective resistance of the sensor mat due to the movement of human on bed.

Larger movement changes the area of coverage of each sensor node more, and larger movement may toggle the electrical contact status of the sensor nodes. Thus, amplitude of change of the overall resistance of the sensor mat is in direct proportion to the amplitude of movement. Therefore, amplitude of the AC signal component is in direct proportion to the amplitude of the movement according to the formula as stated above.

The central processing unit dispatches the following events message to caregivers according to the combined conditions of both outputs of ADC-A and ADC-B:

| Event Message | Condition of ADC-A | Condition of ADC-B |
|---|---|---|
| Human present | Voltage is below threshold value | Ignored |
| Human absent | Voltage is returned to the open circuit value | Ignored |
| Service is required | Any voltage lies between the upper ceiling and the lowest boundary of the threshold value. | Ignored |
| Movement detect | Voltage is below threshold value | AC signal with amplitude larger than the preset threshold. |

From the above list, the MCU detects the presence of human by measuring voltage value from output port of the first ADC unit which is below the preset threshold voltage level of open circuit condition and lasts for the preset interval of time. The MCU detects the absence of human by measuring voltage value from output port of the first ADC unit which returns to the preset threshold voltage level of open circuit condition and lasts for the preset interval of time. The MCU detects the movement of human by voltage value from output port of the first ADC unit which is below the preset threshold voltage level of open circuit condition and measuring amplitude of the AC signal from output port of the second ADC unit. The MCU detects the voltage value from output port of the first ADC unit which is within the preset threshold voltage level of open circuit condition, the service is required.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

What is claimed is:

1. A multi-zone pressure sensitive mat comprises a first electrode and a second electrode, wherein:
    the first electrode connects to an input port of a central processing unit and the second electrode connects to the digital ground return port of the central processing unit;
    the central processing unit comprises at least one micro controller unit (MCU), the MCU comprises a first analog to digital conversion (ADC) unit and a second ADC unit, wherein electrical signal from the input port is split into original DC signal and its AC signal, wherein the DC signal is fed into the first ADC unit from the input port, the AC signal is bypassed through a capacitor from the input port, filtered through a low pass filter (LPF), amplified through an amplifying circuit and fed into the second ADC unit; wherein a preset threshold voltage level and a preset interval of time are stored in the MCU;
    the MCU detects the presence of human by measuring voltage value from output port of the first ADC unit which is below the preset threshold voltage level of open circuit condition and lasts for the preset interval of time; and
    the MCU detects the absence of human by measuring voltage value from output port of the first ADC unit which returns to the preset threshold voltage level of open circuit condition and lasts for the preset interval of time.

2. The multi-zone pressure sensitive mat of claim 1, wherein the MCU detects the movement of human by voltage value from output port of the first ADC unit which is below the preset threshold voltage level of open circuit condition and measures amplitude of the AC signal from output port of the second ADC unit.

3. The multi-zone pressure sensitive mat of claim 2, wherein the amplitude of the AC signal is in direct proportion to the amplitude of the movement.

4. The multi-zone pressure sensitive mat of claim 1, wherein a calibration routine is built in the MCU; and
    wherein the MCU detects the voltage value from output port of the first ADC unit which is within the preset threshold voltage level of open circuit condition, the calibration is required.

5. The multi-zone pressure sensitive mat of claim 4, wherein through running the calibration routine, the threshold voltage level stored in the MCU is refreshed with the new measurement which is derived from the resistance of the overall circuit.

6. The multi-zone pressure sensitive mat of claim 1, wherein the multi-zone pressure sensitive mat comprises a multi-zone passive pressure sensor, wherein the passive pressure sensor comprises a top sensors matrix, a middle flexible insulation spacer and a bottom sensors matrix, wherein the top sensors matrix is a top layer of variable resistance sensors row matrix and the bottom sensors matrix is a bottom layer with variable resistance sensors column matrix.

7. The multi-zone pressure sensitive mat of claim 6, wherein the top sensors matrix and the bottom sensors matrix are comprised of a flexible thermoplastic membrane serve as a substrate for an electrical circuit, and the electrical circuit on the top sensor matrix and the bottom sensor matrix are comprised of electrical tracks, embedded resistors and variable resistance sensor nodes.

8. The multi-zone pressure sensitive mat of claim 7, wherein the flexible thermoplastic membrane is polyethylene terephthalate sheet (PET).

9. The multi-zone pressure sensitive mat of claim 7, wherein the electrical circuit is formed by printing the whole pattern of the circuit using a uniform layer of Polymer Thick Film (PTF) carbon ink over the substrate.

10. The multi-zone pressure sensitive mat of claim 9, wherein the value of resistance of a particular segment of printed PTF carbon track is specified by the effective length and the overall width of the pattern of the track; and an embedded resistor with specific resistance value is fabricated by printing a continuous PTF carbon track or a combination of multiple PTF carbon tracks over the substrate.

11. The multi-zone pressure sensitive mat of claim 10, wherein the value of resistance of a particular segment of printed PTF carbon track follows the equation:

$$Rt = Rs(L/W)^2$$

wherein:
Rt is Resistance of the track segment in [$\Omega$];
Rs is Sheet Resistivity in [$\Omega/mm^2$];
L is Length in [mm];
W is Width in [mm].

12. The multi-zone pressure sensitive mat of claim 11, wherein both ends of the printed pattern of PTF carbon tracks serve as the terminals of the effective embedded resistor; and the embedded resistors connect to the printed circuit with PTF carbon ink of same uniform composition over the whole printed circuit.

13. The multi-zone pressure sensitive mat of claim 7, wherein the variable resistance sensor node is comprised of a top contact pad and a bottom contact pad, the top contact pad and the bottom contact pad are fabricated by printing with PTF carbon ink of same uniform composition over the whole printed circuit, and a corresponding opening on middle flexible spacer allows the top contact pad comes into electrically contact with the bottom contact pad when weight or pressure is applying on the area of the corresponding opening.

14. The multi-zone pressure sensitive mat of claim 13, wherein effective value of resistance of each variable resistance sensor node is in indirect proportion to the area of physical contact between the top contact pad and the bottom contact pad.

15. The multi-zone pressure sensitive mat of claim 1, wherein an open circuit voltage level is defined in the hardware circuit with a pull-up resistor connect input of the first ADC unit to the power supply of the circuit, under the condition that the circuit between the first ADC unit and the ground is opened.

16. The multi-zone pressure sensitive mat of claim 15, wherein the MCU filters out noisy signal by monitoring the consistency of the measured voltage level from input of the first ADC unit; and signal with fluctuation along the preset threshold value of open circuit condition is ignored.

17. The multi-zone pressure sensitive mat of claim 1, wherein the MCU detects movement of the human on bed by measuring the amplitude of the AC signal from the output of the second ADC unit; and the AC signal component is derived from the change of resistance of each sensor node.

18. The multi-zone pressure sensitive mat of claim 17, wherein the electrical circuit is equivalent to a variable resistor when any one or multiple of the sensor nodes come into electrical contact.

19. The multi-zone pressure sensitive mat of claim 18, wherein an equivalent voltage divider circuit comprises a pull-up resistor and the equivalent variable resistor connected across the first electrode and the second electrode of the sensor mat; and Voltage across the first electrode and the second electrode, when the sensor mat is connected to the host MCU circuit, is derived by the formula:

$$V(\text{sensor}) = Vcc(R(\text{sensor mat})/(R(\text{pull-up}) + R(\text{sensor mat})))$$

wherein:
V(sensor) is Input voltage to the first ADC unit across the two electrodes of the sensor mat;
Vcc is Voltage supply to the central processing unit and one end of the pull-up resistor ties to this voltage;
R(pull-up) is Resistance of the pull-up resistor;
R(sensor mat) is Resistance across electrodes of the sensor mat.

* * * * *